(12) United States Patent  
Kunath et al.

(10) Patent No.: US 9,383,334 B2  
(45) Date of Patent: Jul. 5, 2016

(54) ION-SENSITIVE LAYER STRUCTURE FOR AN ION-SENSITIVE SENSOR AND METHOD FOR MANUFACTURING THE SAME

(71) Applicant: Endress + Hauser Conducta Gesellschaft für Mess- und Regeltechnik mbH + Co. KG, Gerlingen (DE)

(72) Inventors: Christian Kunath, Dresden (DE); Eberhard Kurth, Moritzburg (DE); Torsten Pechstein, Radebeul (DE)

(73) Assignee: Endress+Hauser Conducta GmbH+Co. KG (DE)

( * ) Notice: Subject to any disclaimer, the term of this patent is extended or adjusted under 35 U.S.C. 154(b) by 0 days.

(21) Appl. No.: 14/464,268

(22) Filed: Aug. 20, 2014

(65) Prior Publication Data

US 2015/0060953 A1 Mar. 5, 2015

(30) Foreign Application Priority Data

Aug. 29, 2013 (DE) .......................... 10 2013 109 357

(51) Int. Cl.
*G01N 27/414* (2006.01)
*H01L 21/28* (2006.01)

(52) U.S. Cl.
CPC ........ *G01N 27/414* (2013.01); *H01L 21/28088* (2013.01); *H01L 21/28229* (2013.01)

(58) Field of Classification Search
CPC ............... H01L 21/28273; H01L 21/823462; H01L 21/823857; H01L 21/28185; H01L 21/02296; H01L 21/02318–21/02323; H01L 21/02356–21/02359; H01L 21/02142–21/02153; H01L 21/02172–21/02189; H01L 21/02107; H01L 21/02123; G01N 27/414
See application file for complete search history.

(56) References Cited

U.S. PATENT DOCUMENTS

| | | | |
|---|---|---|---|
| 3,819,990 A * | 6/1974 | Hayashi et al. | 361/313 |
| 5,288,563 A | 2/1994 | Saito | |
| 6,445,033 B1 * | 9/2002 | Hasegawa | 257/324 |
| 6,645,882 B1 * | 11/2003 | Halliyal et al. | 438/785 |

(Continued)

FOREIGN PATENT DOCUMENTS

| | | |
|---|---|---|
| DE | 102009002060 A1 | 10/2010 |
| DE | 102009028486 A1 | 2/2011 |

(Continued)

OTHER PUBLICATIONS

German Search Report, German PTO, Munich, Feb. 5, 2014.

(Continued)

*Primary Examiner* — William F Kraig
*Assistant Examiner* — Maliheh Malek
(74) *Attorney, Agent, or Firm* — Christopher R. Powers; PatServe

(57) ABSTRACT

In a method for manufacturing an ion-sensitive structure for an ion-sensitive sensor, first a semiconductor substrate bearing an oxide layer is provided, whereupon a metal oxide layer and a metal layer are deposited and tempered, in order to obtain a layer sequence having a crystallized metal oxide layer and an oxidized and crystallized metal layer on the semiconductor substrate bearing the oxide layer. In such case, the metal oxide layer and the metal layer have a compatible metal element, and the coating thickness $d_{MOX}$ of the metal oxide layer is greater than the coating thickness $d_{MET}$ of the metal layer.

25 Claims, 7 Drawing Sheets

(56) References Cited

U.S. PATENT DOCUMENTS

| | | | |
|---|---|---|---|
| 6,737,716 B1* | 5/2004 | Matsuo et al. | 257/406 |
| 7,321,143 B2* | 1/2008 | Kunath et al. | 257/288 |
| 7,355,200 B2* | 4/2008 | Kurth et al. | 257/48 |
| 7,481,882 B2* | 1/2009 | Won et al. | 117/97 |
| 7,579,231 B2* | 8/2009 | Matsuo et al. | 438/216 |
| 8,288,297 B1* | 10/2012 | Wang | C23C 16/40 257/E21.159 |
| 8,461,587 B2 | 6/2013 | Kurth | |
| 8,519,447 B2 | 8/2013 | Zeun | |
| 2001/0015453 A1* | 8/2001 | Agarwal | 257/310 |
| 2001/0023120 A1* | 9/2001 | Tsunashima et al. | 438/585 |
| 2002/0106536 A1* | 8/2002 | Lee et al. | 428/702 |
| 2003/0075740 A1* | 4/2003 | Bai et al. | 257/216 |
| 2004/0102002 A1* | 5/2004 | Sandhu et al. | 438/240 |
| 2004/0183142 A1* | 9/2004 | Matsuo et al. | 257/406 |
| 2005/0012115 A1* | 1/2005 | Grueger et al. | 257/192 |
| 2005/0263798 A1* | 12/2005 | Kurth et al. | 257/253 |
| 2006/0035420 A1* | 2/2006 | Kunath | G01N 27/414 438/151 |
| 2006/0062917 A1* | 3/2006 | Muthukrishnan et al. | 427/248.1 |
| 2007/0057333 A1* | 3/2007 | Park et al. | 257/411 |
| 2007/0134942 A1* | 6/2007 | Ahn et al. | 438/785 |
| 2009/0014757 A1* | 1/2009 | Takulapalli et al. | 257/253 |
| 2009/0096008 A1* | 4/2009 | Kim et al. | 257/316 |
| 2009/0124070 A1* | 5/2009 | Yoo et al. | 438/591 |
| 2009/0170341 A1* | 7/2009 | Kitano et al. | 438/770 |
| 2009/0230391 A1* | 9/2009 | Noshiro | 257/43 |
| 2010/0044798 A1* | 2/2010 | Hooker et al. | 257/369 |
| 2011/0031986 A1* | 2/2011 | Bhat | G01N 27/4143 324/686 |
| 2011/0048769 A1* | 3/2011 | Fujiwara | 174/137 B |
| 2012/0001172 A1* | 1/2012 | Shang | C01G 19/02 257/43 |
| 2012/0018722 A1* | 1/2012 | Kurth et al. | 257/43 |
| 2012/0025297 A1* | 2/2012 | Takashima et al. | 257/324 |
| 2012/0052645 A1* | 3/2012 | Haneda | 438/287 |
| 2012/0088360 A1* | 4/2012 | Kim et al. | 438/592 |
| 2012/0139011 A1* | 6/2012 | Zeun | 257/253 |
| 2012/0262835 A1* | 10/2012 | Ramani | H01L 28/60 361/271 |
| 2012/0292585 A1* | 11/2012 | Cheung | H01L 27/101 257/2 |
| 2012/0309163 A1* | 12/2012 | Kiyomura et al. | 438/396 |
| 2013/0056702 A1* | 3/2013 | Wang | C23C 16/40 257/4 |
| 2013/0109147 A1* | 5/2013 | Rocklein | H01L 45/08 438/381 |
| 2013/0186178 A1* | 7/2013 | Usagawa | B82Y 15/00 73/31.06 |
| 2013/0200491 A1* | 8/2013 | Wamura et al. | 257/532 |
| 2013/0313569 A1* | 11/2013 | Usagawa | H01L 29/78 257/77 |
| 2014/0151710 A1* | 6/2014 | Lin et al. | 257/76 |
| 2015/0140773 A1* | 5/2015 | Antonov | H01G 4/306 438/381 |

FOREIGN PATENT DOCUMENTS

| | | | |
|---|---|---|---|
| WO | 2004044572 A1 | 5/2004 | |
| WO | 2005073706 A1 | 8/2005 | |

OTHER PUBLICATIONS

P. Bergveld, "Development of an Ion-Sensitive Solid-State Device for Neurophysiological Measurements" IEEE Trans. Biomed. Eng. BME-17 (Jan. 1970).

P.V. Bobrov et al. "Chemical Sensitivity of an ISFET with $Ta_2O_5$ Membrane in Strong Acid and Alkaline Solutions", Leningrad State University, USSR and Humboldt Univ., Berlin, Germany, Sensors and Actuators B,3 (1991) pp. 75-81.

T. Mikolajick, et al., "The pH-Sensing Properties of Tantalum Pentoxide Films Fabricated by Metal Organic Low Pressure Chemical Vapor Deposition", Fraunhofer Institute Integrated Circuits, Device Technology (IIS-B), Erlangen, Germany, (1997), pp. 262-267.

Jung-Chuan Chou et al., "Sensitivity and Hysteresis Effect in $Al_2O_3$ Gate pH-ISFET", Dept. of Electronic Engineering, National Yunlin University of Science and Technology, Taiwan, Materials Chemistry and Physics 71 (2001), pp. 120-124.

Jung Chuan Chou et al., "Study of $TiO_2$ Thin Films for Ion Sensitive Field Effect Transistor Application with RF Sputtering Deposition", Institute of Electronic and Information Engineering, National Yunlin University of Science & Technology, Taiwan, Japanese Journal of Applied Physics, vol. 43, No. 1, 2004, pp. 61-65.

Shoji Yoshida et al., "Development of a Wide Range pH Sensor based on Electrolyte-Insulator-Semiconductor Structure with Corrosion-Resistant $Al_2O_3$-$Ta_2O_5$ and $AlO_3$-$ZrO_2$, Double-Oxide Thin Films", Dept. of Metallurgy, Tohoku Univ., Journal of the Electrochem. Soc. 151(3) H53-H58 (2004).

Cho-Sung Lai et al., "pH Sensitivity Improvement on 8 nm Thick Hafnium Oxide by Post Deposition Annealing", Dept. of Electronic Engineering, Chang Gung Univ., Taiwan, Electrochemical and Solid State Letters 9(3) G90-2 (2006).

P.D. Van Der Wal et al., "High-K Dielectrics for Use as ISFET Gate Oxides", IEEE Sensors (2004), p. 677.

* cited by examiner (optional)

(optional)

(Option I)

(Option II)

(optional)

ION-SENSITIVE LAYER STRUCTURE FOR AN ION-SENSITIVE SENSOR AND METHOD FOR MANUFACTURING THE SAME

TECHNICAL FIELD

The present invention relates generally to ion-sensitive sensors and their manufacture and especially to an ion-sensitive, multilayer, metal oxide structure for an ion-sensitive sensor, as well as to a method for manufacturing same, wherein applicable as ion-sensitive sensors are e.g. ion-sensitive field effect transistors (ISFETs), ion-sensitive, capacitively readable EIS sensors and LAPS sensors.

BACKGROUND DISCUSSION

Ion-sensitive sensors having an electrolyte insulator semiconductor structure (EIS structure), especially ion-sensitive field effect transistors (ISFETs), ion-sensitive, capacitive, respectively capacitively readable, sensors having an EIS structure or light operated, ion-sensitive LAPS sensors (LAPS=Light Addressable Potentiometric Sensor) having an EIS structure, are applied for measuring ion concentrations or special substance concentrations in solutions of different compositions and conductivities. Applications of ion-sensitive sensors with ISFETs, EIS elements and LAPS elements for the continuous checking of concentrations exist, for example, in the fields of environmental monitoring, industrial process monitoring, the foods industry and biochemistry, respectively medical technology. In such case, especially an as exact as possible concentration registration exhibiting an as small as possible, long term drift of the sensor element combined with an acceptable purchase price are desired for a corresponding ion-sensitive sensor.

Used as semiconductor material for the respective EIS structures, respectively EIS elements, is frequently silicon (Si), so that silicon dioxide (SiO2) is used as a first insulation layer. Other semiconductor/insulator combinations can frequently not deliver comparable properties as regards the required measurement accuracies during the required lifetime and are, furthermore, frequently not stably reproducible. Traditionally, ion concentration measurements in aqueous media are performed with glass electrodes both in process measurements technology as well as also in laboratory measurements technology. For technical reasons, especially because a sufficiently large inner buffer volume is required coupled with a sufficiently stable glass membrane, there is no opportunity for an efficient miniaturization of conventional glass electrodes. Moreover, it is to be noted that a pH-measuring system using a glass electrode has high impedance due to the needed glass membrane thickness and, thus, reacts sensitively to electrical environmental disturbances. This requires, among others, a shielding of the measuring lines, wherein the separation between the electrode and the measuring device should be as small as possible.

A further inherent disadvantage of the application of glass electrodes for pH-measuring is that, due to the application of the material, glass, there is a glass breakage risk under certain conditions, so that the use of glass electrodes in certain fields, such as e.g. foods technology, etc., is only limitedly possible.

For this reason, it is, consequently, attempted to use ion-sensitive EIS structures, respectively EIS elements, especially in the form of field effect transistors (ISFETs), for ion concentration measurement, such as e.g. for measuring pH-value in aqueous media [1], wherein the use of such ion-sensitive sensors has increased somewhat in the last years in industry by applying EIS structures. Ion-sensitive sensors having an EIS structure are suitable for miniaturizing a measuring system especially through the relatively cost effective manufacture of integrated systems and are especially superior to the application of conventional glass electrodes. Thus, instead of the inner buffer with glass interface, a well manageable Si/SiO2 combination is utilized. A further advantage of the sensors based on EIS structures is that such can be produced without the material, glass, whereby the requirement is met that in the case of some applications a glass breakage risk is not desired, respectively necessarily must be avoided.

Expressed generally, an ISFET sensor can be viewed as an impedance converter integrated in the sensor, which represents a still higher impedance of the EIS structure than that of a glass electrode, wherein, however, the measured variable is converted directly on-site into an easily and precisely measurable, low impedance signal. Through the application of the operating mode ("constant charge"), an ISFET sensor is, furthermore, able to suppress signal disturbances due to environmental light, respectively ambient light, relatively well.

A capacitively readable EIS sensor without FET structure can, for example, be so constructed that no topology edges disturb the surface, respectively the surface character, so that the risk of action of chemically aggressive media on possible topology edges can be lessened. The read-out of such an EIS sensor occurs, for example, via a capacitance measurement.

The LAPS sensors (LAPS=Light Addressable Potentiometric Sensor) make use of sensitivity resolved laterally along the surface and are suited, for example, for biochemical systems, wherein the region to be detected can be selectively irradiated with light [13].

Since the previously achieved chemical and electrical, long term stability of ion-sensitive sensors based on EIS structures is still not sufficient for use in process measurements technology, respectively corresponding ion-sensitive sensors are extremely complex and therewith expensive to manufacture, previously no lasting introduction of EIS-based pH-measuring could occur in industrial process measurements technology and in environmental monitoring.

SUMMARY OF THE INVENTION

Proceeding from this state of the art, thus, an object of the present invention is to provide an as uncomplicated as possible procedure for arrangement and manufacture of an ion-sensitive structure for ion-sensitive sensors, with which both an as great as possible chemical and electrical, long term stability as well as also extremely exact and reproducible measurement results can be obtained.

This object is achieved by a method for manufacture of an ion-sensitive structure for an ion-sensitive sensor, by a method for manufacture of an ion-sensitive field effect transistor, by a method for manufacture of an ion-sensitive, capacitively readable sensor, by a method for manufacture of a light operated, ion-sensitive sensor having an ion-sensitive structure, and by an ion-sensitive sensor having an ion-sensitive structure.

The present invention is based on the recognition that a both chemically as well as also electrically, extremely long term stable, ion-sensitive structure for an ion-sensitive sensor can be produced by applying as insulator on a semiconductor material, respectively semiconductor substrate, which comprises, for example, n- or p doped silicon, an insulation layer, e.g. an $SiO_2$ layer, by thermal oxidation (e.g. an amorphous layer), wherein on the oxide layer, in turn, a double layer, respectively a plurality of double layers, having a metal oxide layer and a metal layer is deposited and tempered, in order to obtain a layer sequence, respectively double layer (or a plurality of double layers), having a crystallized metal oxide layer and an oxidized and crystallized metal layer on the semiconductor substrate bearing the oxide layer. In such case, the metal oxide layer and the metal layer are so deposited that the coating thickness of the metal oxide layer $d_{MOX}$ is (markedly) greater than the coating thickness $d_{MET}$ of the metal layer arranged thereon. Furthermore, the applied metal oxide layer and the thereon deposited metal layer have a compatible metal element, respectively the same metal element.

The oxide layer applied, for example, by thermal oxidation, on the semiconductor substrate has, for example, a thickness $d_{OX}$ of 3 to 150 nm. The metal oxide layer, which acts as a so-called buffer layer, is applied on the oxide material with a thickness $d_{MOX}$, for example, of 50 to 200 nm, while the metal layer is applied on the metal oxide layer, respectively buffer layer, with a coating thickness $d_{MET}$ of, for example, 3 to 30 nm.

In the present invention, thus, the metal layer to be thermally oxidized is not directly applied onto the oxide layer, respectively insulation layer, provided on the semiconductor substrate, but, instead, a metal oxide layer acting as buffer layer is first applied, respectively deposited, on the oxide layer, before, in a following metal deposition, the metal layer is applied on the already deposited metal oxide layer. For example, the application and thermal treatment of a double layer having a metal oxide layer and a metal layer arranged thereon can be repeated a number of times, in order to obtain a plurality of double layer sequences with, in each case, a metal oxide layer and a metal layer arranged thereon.

As subsequently will be explained in greater detail, in the case of the manufacturing process of the invention, after the respective applying or depositing of the individual layers, i.e. the metal oxide layer(s) or metal layer(s), in each case, an oxidative tempering, or heat treatment, and/or a crystallization tempering, or heat treatment, can be performed, in order to subject the, in each case, individually present, e.g. amorphous, layers to an oxidative- and/or crystallization tempering, in order, in each case, to obtain a metal oxide layer or a metal layer having an oxidized and/or crystallized structure. Equally, an option is to apply a double layer, respectively a number of double layers, of the metal oxide material and the metal material and to perform an oxidative tempering and/or crystallization tempering on the as yet thermally untreated layer sequence, respectively double layer sequence (or the plurality of double layers).

In the context of the present description, in general, by way of example, the application and thermal treatment of a double layer having a metal oxide layer and a metal layer arranged thereon is described. These explanations are, however, equally applicable to a manufacturing procedure, in the case of which a plurality of double layer sequences with, in each case, a metal oxide layer and a metal layer arranged thereon are produced one after the other.

Through the application and tempering of the invention of a relatively thick buffer layer, respectively metal oxide layer, and the metal layer, which have the same one or more metal elements, it can be prevented that, through the metal deposition of the metal layer and its thermal treatment for an oxidation, the material of the oxide layer is damaged, i.e., for example, a damaging of the $SiO_2$ material of the gate insulator can be prevented or at least lessened.

Furthermore, the metal oxide layer acting as buffer layer is produced with a sufficiently large coating thickness to achieve that residual interface charges and traps, which remain after the oxidation and tempering of the metal material of the metal layer in, respectively on, the interface between the metal oxide layer and metal layer, occur (relatively) widely removed from the semiconductor/insulator interface. The metal oxide layer is thus effective to function as a buffer layer, respectively spacing layer, between the insulation layer and the trap- and/or charge bearing interface between the metal oxide layer and the metal layer.

By means of the ion-sensitive structure, respectively ion-sensitive EIS structure, of the invention, as compared with the previously used materials, an increased stability and sensitivity is obtained as regards the ions to be detected, wherein, furthermore, low cross-sensitivity and minimal drift coupled with good long term stability of a correspondingly formed sensor is achieved. Thus, the vertical, respectively global, grain boundaries, which thermal treatments (tempering) lead to between the gate electrolyte interface and the insulation layer (gate insulator, e.g. $SiO_2$), respectively the semiconductor bulk material (e.g. Si), can be prevented, respectively interrupted, as much as possible by the ion-sensitive EIS structure manufactured according to the invention.

In the following, based on further documentation of the state of the art, critical properties of conventional EIS structures will now be explored, wherein, furthermore, the findings and inventive conclusions of the inventors will be brought out taking into consideration the object underlying the present invention.

For manufacturing hydrogen ion sensitive layers, various materials, such as e.g. $Ta_2O_5$ [2], [3], $Al_2O_3$ [4], $TiO_2$ [5], $HfO_2$ [8] and simple metal nitrides [10], or double metal oxide mixtures such as e.g. TaAlO and ZrAlO [6], or combinations of two different amorphous metal oxide layers [11], and diamond-like carbon (DLC) [9] have been examined and described. With few exceptions [7], these almost always lie on $SiO_2$. With the introduction of metal oxides, clear improvements of the sensor characteristics, such as pH-sensitivity, long term stability and drift of these sensors were achieved compared with the $Si_3N_4$ ISFETs.

With the introduction of metal oxides as sensitive layer material, clear improvements of the application fields relative to pH ranges and media temperatures could be achieved. The conventional metal oxides are deposited amorphously and only tempered to an extent that their amorphous structure remains. These structures are, however, chemically non-resistant and are subject at increased temperature in corrosive media to planar etching.

Simple crystalline metal oxide layers are as chemically resistant as amorphous layers, since the crystallites have a high density comparable with the bulk material. The weak point of these layers are the grain boundaries, especially the vertical grain boundaries, which permit pore etching and subsequently an under etching in the case of higher temperatures in aggressive media. Thus, a stable operation of $Ta_2O_5$ ISFETs up to a pH-value of about 12 and a temperature up to 75° C. is achieved.

In the case of multilayer depositions of polycrystalline metal oxides, however, the vertical grain boundaries are only insufficiently interrupted, since the crystals of the first layer function as growth nuclei for the second layer. At the interface between the crystalline layers, traps and charges are very easily collected, whereby, however, the working point of an ISFET becomes poorly reproducible.

The deposition of metals and subsequent thermal oxidation [12] leads, as a result of kinetics, to a poor quality of the gate insulator, since the material, beginning from contact and as a result of heating increasingly takes the oxygen partially from the underlying gate insulator.

In the measuring methodology of LAPS elements (LAPS=Light Addressable Potentiometric Sensor) a modulated light signal is introduced into the EIS structure and there produces photoelectrons. The production of the photoelectrons is also controlled by the properties of the electrolyte [13]. In the measuring methodology of the EIS elements, the capacitance of the EIS structure is controlled with electrical voltage without light supply. The capacitance is also controlled by the characteristics of the electrolyte.

Since the previously achieved chemical and electrical stability in the case of chemical and thermal sterilization is still not sufficient for use in process measurements technology, there has been no lasting introduction of EIS-based pH-measurement in industrial process measurements technology and in environmental monitoring.

BRIEF DESCRIPTION OF THE DRAWINGS

Preferred examples of embodiments of the present invention will now be explained in greater detail with reference to the appended drawing, the figures of which show as follows.

DETAILED DISCUSSION IN CONJUNCTION WITH THE DRAWINGS

Figure 1A:
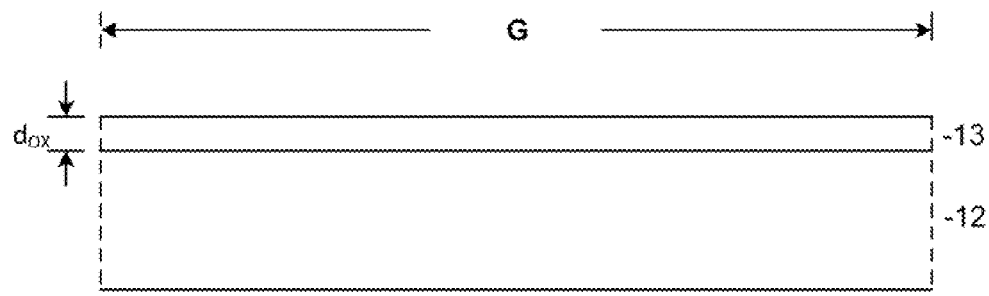
FIGS. 1a-1g are, by way of example, a representation in principle of a process sequence for manufacturing an ion-sensitive, multilayered sensor structure for an ion-sensitive sensor according to an example of an embodiment of the present invention.

Before explaining the present invention in greater detail based on the drawings, it is noted that identical, functionally equal or equally acting elements or structures are provided in the various figures with equal reference characters, so that the descriptions in the different examples of embodiments for elements or structures provided with equal reference characters are exchangeable with one another, respectively can be applied to one another.

In the following by way of example, based on a process sequence illustrated, in principle, in FIGS. 1a-g, a method for manufacturing an ion-sensitive, multilayered sensor structure for an ion-sensitive sensor according to an example of an embodiment of the present invention will now be described. The following explanations show, furthermore, that the different process steps can occur, for example, in the context of a CMOS process.

As shown in FIG. 1a, for example, a semiconductor substrate 12, e.g. an n- or p doped silicon substrate, having located thereon an oxide layer 13 (insulation layer or insulator layer), e.g. a silicon dioxide layer ($SiO_2$), is provided. Insulation layer 13 is produced on the semiconductor substrate 12, for example, by thermal oxidation at a temperature of up to about 1100° C. The thermally produced insulation layer 13 has, for example, amorphous material properties and a coating thickness $d_{OX}$ of 3-150 nm. As further shown in FIG. 1a, the section shown in FIGS. 1a-g concerns, for example, a lateral extent of the gate section G for the case of application of the ion-sensitive layer structure of the invention for an ISFET, such as this is described in detail, for example, subsequently with respect to FIGS. 4a-b. The region G shown in FIGS. 1a-g for the ion-sensitive structure is, however, equally applicable to sections of ion-sensitive, capacitively readable EIS sensors or also LAPS sensors. Thus, for example, the region G in FIGS. 1a-g can be the media contacting region of the respective ion-sensitive layer structure in a corresponding ion-sensitive component.

Figure 1B:
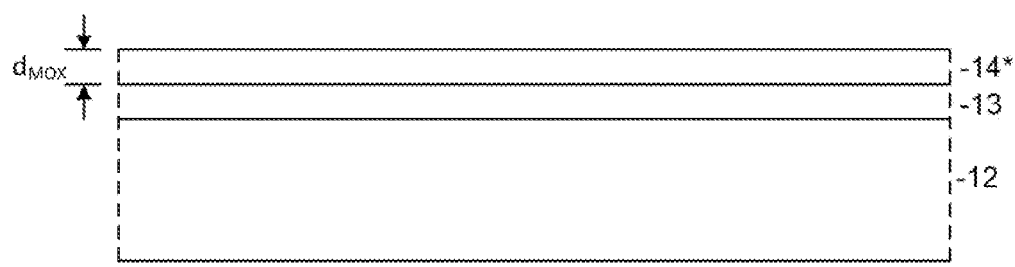
Figure 1C:
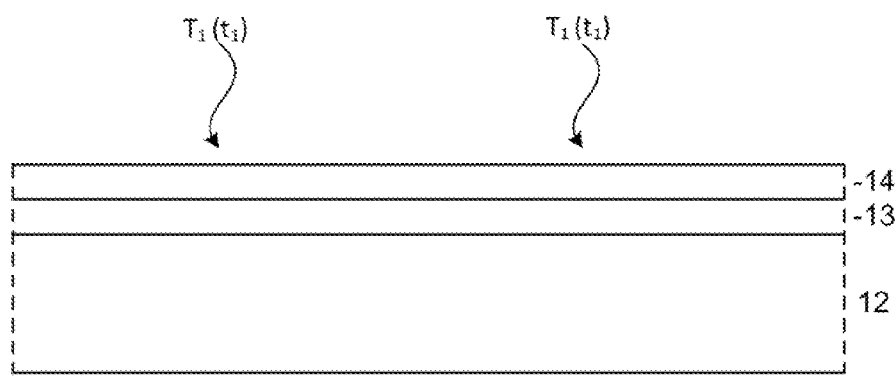
Figure 1D:
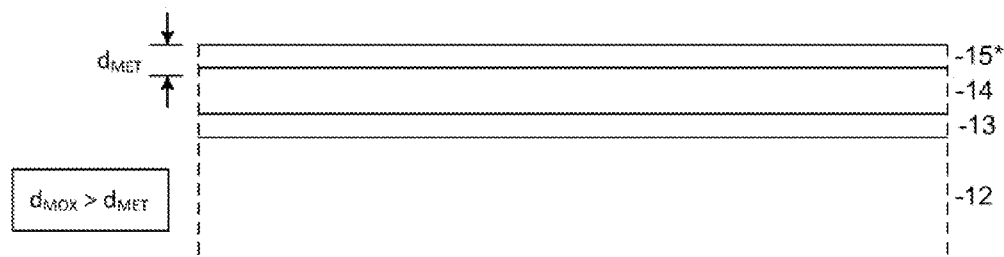
Figure 1E:
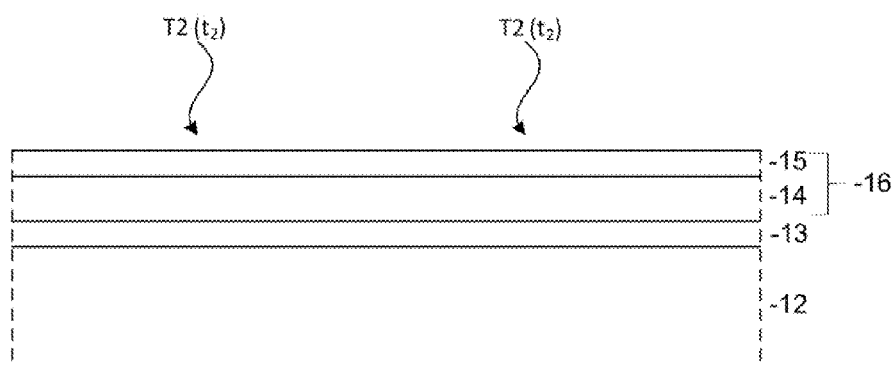

FIG. 1b shows now the applying of a metal oxide layer 14* (respectively, an already applied, amorphous metal oxide layer 14*) having a coating thickness $d_{Mox}$. The e.g. amorphous deposition of the metal oxide layer 14*, which acts as buffer layer, such as will be discussed below, occurs, for example, with a thickness of 25- 400 nm, preferably, for example, 50- 200 nm. Used as the metal oxide material for the metal oxide layer 14* can be, for example, $Ta_2O_5$, $Al_2O_3$, $TiO_2$, $ZrO_2$ or $HfO_2$, wherein this is not an exclusive listing, but, instead, is given only by way of example. Metal oxide layer 14*, as applied on the insulation layer 13 provided on the semiconductor substrate 12, is next subjected to a thermal treatment at a temperature $T_1$ of e.g. greater than 600° C. (e.g. 600°-1000° C.) for a duration $t_1$ of e.g. 10-300 seconds by means of an RTA procedure (RTA=Rapid Thermal Annealing), in order to crystallize the applied metal oxide layer 14*, wherein the so thermally treated metal oxide layer 14 has an at least partially crystalline structure. Applied on the crystallized metal oxide layer 14 is next an e.g. metal layer 15* having a coating thickness dMET of 1-100 nm, preferably, for example, 3-30 nm. Used as metal element for the metal layer 15* can be, for example, tantalum, hafnium, zirconium, titanium or aluminum, wherein this listing of metal elements is only by way of example and not an exclusive listing.

Thereupon, the metal material of the metal layer 15* is subjected to a thermal treatment at a temperature $T_2$ of, for example, greater than 600° C. (e.g. 600°–1000° C.) for a duration $t_2$ of e.g. 10-300 seconds again by means of an RTA procedure, in order thermally to oxidize and crystallize the originally applied metal layer 15*, in order to obtain a thermally oxidized and crystallized metal layer 15 on the crystallized metal oxide layer 14. The metal oxide layer 14 and the metal layer 15, as applied (deposited) and thermally treated on the insulation layer 13 provided on the semiconductor substrate 12, thus form the layer sequence, respectively double layer 16, of the invention as ion-sensitive layer structure for an ion-sensitive sensor.

Figure 1F:
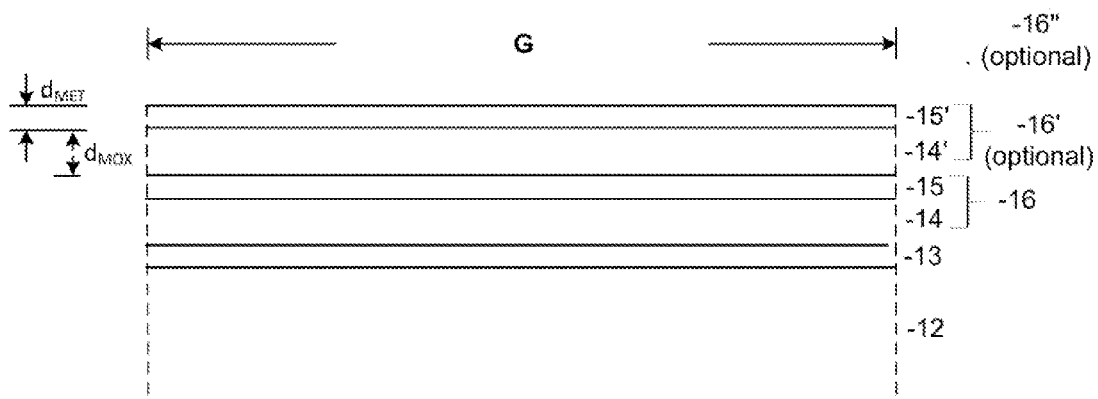

FIG. 1f shows an optional process step. Thus, corresponding to the procedure for producing the layer sequence, respectively double layer 16, illustrated in FIGS. 1b-e, correspondingly, one more or a plurality of additional double layers 16', 16" of a crystallized metal oxide layer 14', 14" and an oxidized and crystallized metal layer 15', 15" can be applied on the double layer 16.

Regarding the process steps illustrated based on FIGS. 1a-f, it should be heeded that the metal oxide layer(s) are, in each case, applied with a coating thickness $d_{MOX}$, which is (markedly) greater ($d_{MOX} > d_{MET}$) than the coating thickness of the respectively thereafter applied metal layer $d_{MET}$. Furthermore, the metal oxide layer(s) and the metal layer(s) have a compatible metal element (e.g. the same metal element). The coating thickness $d_{MOX}$ is, for example, greater than 5 times ($d_{MOX} > 5 \cdot d_{MET}$) or 10 times ($d_{MOX} > 10 \cdot d_{MET}$) the coating thickness $d_{MET}$ of the respectively thereafter applied metal layer.

The metal oxide layer(s) and the metal layer(s) can be applied, for example, by sputtering, vapor deposition, a CVD process (CVD=Chemical Vapor Deposition=chemical gas phase deposition), a PVD process (PVD=Physical Vapor Deposition) or an ALD process (ALD=Atomic Layer Deposition).

Optionally, after termination of the oxidative- and crystallization thermal treatments, a thermal post-treatment (an annealing procedure) can be performed, e.g. with an annealing temperature lower than the crystallization temperatures Ti, respectively $T_2$, for example, a temperature below 600° C. (e.g. 300°-600° C.), in order to achieve a so-called annealing of the crystalline, respectively crystallized, material structure of the layer sequence(s) 16 (respectively 16', 16"). By means of such an annealing procedure, for example, the concentration of crystal defect locations and/or interstitial elements can be minimized and at least lessened.

Optionally, before a crystallization of the still untempered layer sequence of metal oxide layer and metal layer, a thermal pretreatment with or without oxidation of the metal layer can be performed, wherein an oxidation then only leads to an amorphous metal oxide layer from the metal layer.

In an additional, alternative option not explicitly illustrated in FIGS. 1a-g for a thermal treatment of the layer sequence(s), for example, as a preceding, (first) thermal treatment step, a thermal pretreatment at a temperature of ≤600° C. (e.g. between 300° C. and 600° C.) can be performed, in order, first of all, to homogenize more strongly the layer-wise applied, still untempered materials of the layer sequence and in order, for example, to allow the interfaces between neighboring layers of the double layer(s) to alloy and grow together more strongly with one another. Following this thermal pretreatment step, then the tempering of the layer sequence (or individual layers of the layer sequence) at a higher temperature of greater than 600° C. (e.g. 600° C.-1000° C.) is performed, e.g. by means of one or more RTA processes, in order to crystallize, as homogeneously as possible, the layer sequence, which still has the layer-wise applied materials, and in order to obtain as small as possible, sealedly arranged crystallites of the layer materials of the resulting, crystallized layer sequence, i.e. in order lastly to produce an as homogeneous as possible, polycrystalline structure of the layer sequence.

In the preceding, based on FIGS. 1a-g, the process steps for producing the layer sequence, respectively another or a plurality of additional double layers 16', 16" from a crystallized metal oxide layer 14', 14" and an oxidized and crystallized metal layer 15', 15" on the double layer 16 were described. As presented in FIG. 1g as an optional further process step, a terminating protective layer 17 of a metal oxide material can now be deposited on the previously applied layer sequence of one or more double layers 16, respectively 16', 16", etc. In such case, this (thin) metal oxide, protective layer 17 can be deposited directly on the last metal layer 15, respectively 15', 15", etc. of the layer sequence 16, respectively 16', 16", etc., after these metal layers have been emplaced, i.e. in situ, without that this last metal layer was previously tempered. The thickness of the additional metal oxide, protective layer 17 can be between 3 and 70 nm (or also between 3 and 50 nm).

Optionally, the protective layer 17 deposited as metal oxide can be deposited on the last metal layer oxidized, respectively oxidized and crystallized, by a thermal treatment, wherein the metal oxide, protective layer 17 can have a thickness between 3 nm and 70 nm (or also between 10 and 70 nm).

The applied, thin metal oxide, protective layer 17 and the last metal layer, respectively metal oxide layer, contain, in such case, a compatible (respectively the same) metal element.

The providing of the metal oxide, protective layer 17 can affect the operating properties of an ion-sensitive layer structure for an ion-sensitive sensor positively for the following reasons. If, for example, metal layers are produced in a facility and then brought from the process chamber into room air, it is possible, as a function of different parameters, that so-called air oxide films of different composition form. This occurrence limits reproducibility for productive manufacture of ion-sensitive sensors. Such parameters are, for example, air composition, air temperature, duration between deposition and air contact, etc.

In the case of most metals layer deposition processes, which take place in process chambers, in which the oxygen partial pressure is less than in the surrounding air, automatically after leaving the process chamber (thus always), there forms on the last metal layer, among other things, at least one supplemental surface oxide, which is referred to as a so-called air oxide, respectively an air oxide layer. In general, this surface oxide material has a different stoichiometry and structure than would be the case, if a metal oxide layer had been deposited already in the process chamber on the last metal layer.

In the case of metals of interest here, the reactivity of the metal surfaces, when these come into the surrounding air, is so high that, besides oxygen, also other air components, such as e.g. air impurities, become incorporated into the forming air oxide material, since the reaction enthalpy with oxygen is higher than with other gases. In this way, the activation energy of the reactions with other gases is always available. The reactivity of clean metal surfaces after their deposition especially in vacuum, i.e. in the case of very small partial pressures of all conceivable gases, is now lessened, when a "clean" metal oxide material (as metal oxide, protective layer 17) having an equal metal element as the last metal layer is applied on this last metal layer 15, respectively 15' etc. before leaving the process chamber. The reaction enthalpy is then released during the deposition, wherein no other/further disturbing element (that could end up as an inclusion in the oxide layer) is present.

In this connection, it is to be noted that in the case of some application examples of surface processing, certain foreign elements are purposefully required, in order to bring about, by doping of the applied layer, desired, respectively predetermined, properties.

In the following by way of example, based on a process sequence illustrated, in principle, in FIGS. 2a-g, a further method for manufacturing an ion-sensitive, multilayered sensor structure for an ion-sensitive sensor according to an additional example of an embodiment of the present invention will be described. The following explanations show that the manufacture of the ion-sensitive structure, respectively EIS layer structure, of the invention for an ion-sensitive sensor can occur, for example, again in a CMOS process.

Figure 2A:
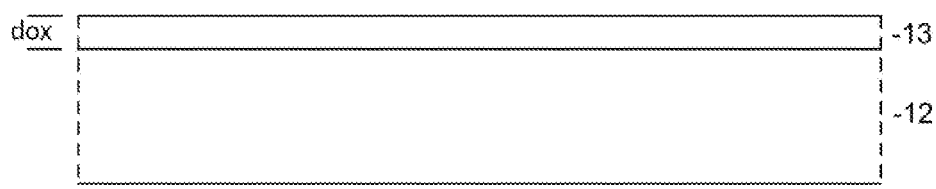
FIGS. 2a-2g are, by way of example, a representation in principle of process sequences for manufacturing an ion-sensitive, multilayered sensor structure for an ion-sensitive sensor according to additional examples of embodiments of the present invention.

As shown in FIG. 2a, for example, a semiconductor substrate 12, e.g. an n- or p doped silicon substrate, is provided bearing an oxide layer 13 (insulation layer or insulator layer), e.g. a silicon dioxide layer ($SiO_2$). Insulation layer 13 is produced on the semiconductor substrate 12, for example, by thermal oxidation at a temperature of up to about 1100° C. The thermally produced insulation layer 13 has, for example, amorphous material properties and a coating thickness $d_{OX}$ of 3-150 nm. As further shown in FIG. 2a, the section shown in FIGS. 2a-g concerns, for example, a lateral extent of the gate section G for the case of application of the ion-sensitive layer structure of the invention in an ISFET, such as this is described in detail, for example, subsequently with respect to FIGS. 4a-b. The region G shown in FIGS. 2a-g for the ion-sensitive structure is, however, equally applicable to sections of ion-sensitive, capacitively readable EIS sensors or LAPS sensors. Thus, for example, the region G in FIGS. 2a-g can be the media contacting region of the respective ion-sensitive layer structure in a corresponding ion-sensitive component.

Figure 2B:
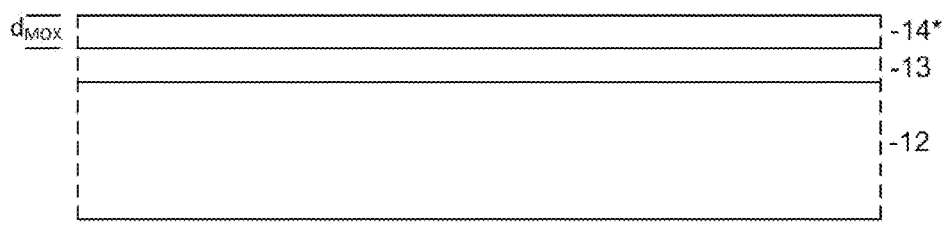
Figure 2C:
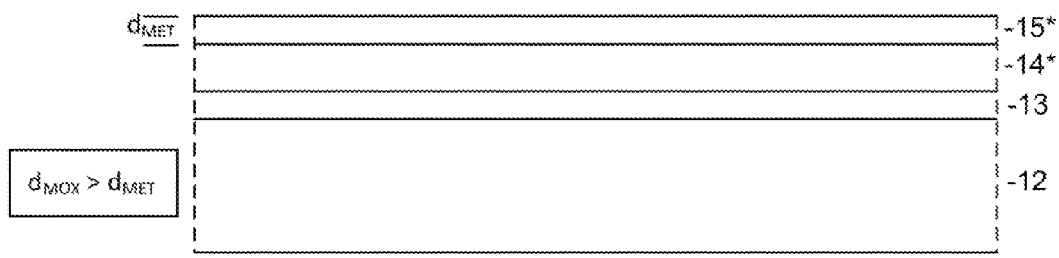

FIG. 2b shows now the applying of a metal oxide layer 14* (respectively, an already applied, amorphous metal oxide layer 14*) with a coating thickness $d_{MOX}$. The deposition of the (e.g. amorphous) metal oxide layer 14*, which acts as buffer layer, such as will be discussed below, occurs, for example, with a thickness of 25-400 nm, preferably, for example, 50-200 nm. Used as the metal oxide material for the metal oxide layer 14* can be, for example, $Ta_2O_5$, $Al_2O_3$, $TiO_2$, $ZrO_2$ or $HfO_2$, wherein this is not an exclusive listing, but, instead, is given only by way of example. Applied on the metal oxide layer 14* is then an e.g. amorphous metal layer 15* having a coating thickness $d_{MET}$ of 1-100 nm, preferably, for example, 3-nm, such as this is shown in FIG. 2c. Used as metal element for the metal layer 15* can be, for example, tantalum, hafnium, zirconium, titanium or aluminum, wherein this listing of metal elements is only by way of example and not an exclusive listing.

In the case of the procedure illustrated based on FIGS. 2a-c, there is thus produced on a semiconductor substrate 12 (e.g. an n- or p doped silicon substrate) as first layer by a thermal oxidation procedure the insulation layer 13 (e.g. an $SiO_2$ layer) as substrate oxide having a coating thickness $d_{OX}$ of 3-150 nm. Thereafter occurs the deposition of the first (e.g. amorphous) metal oxide layer 14*, which acts, for example, as a buffer layer, having a thickness of 50-200 nm, wherein, for example, as metal oxide material, $Ta_2O_5$ is applied on the insulation layer by means of a PVD method. Applied on the metal oxide layer 14* is then the metal layer 15* having a coating thickness of, for example, 3-30 nm, wherein deposited for this is, for example, tantalum as metal material by means of a PVD method.

Figure 2D:
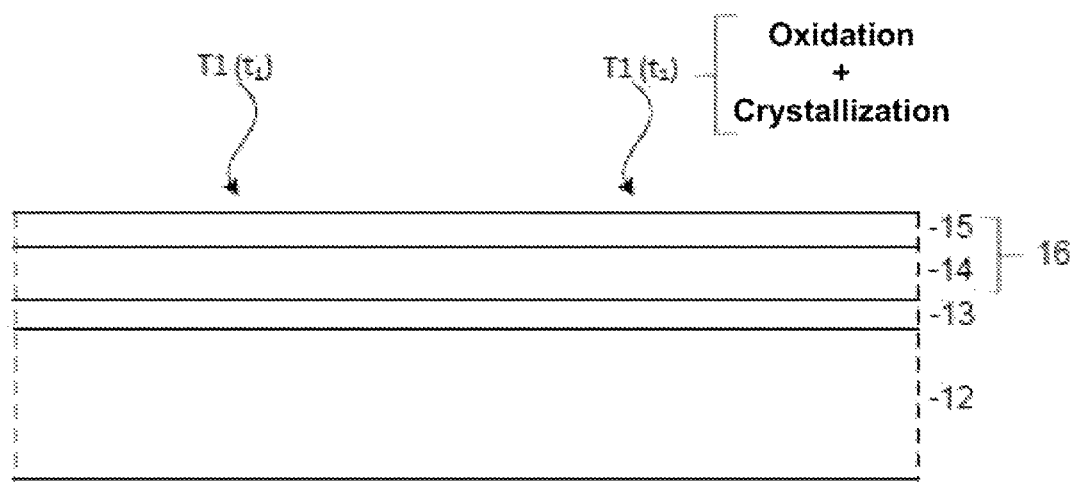

In a first procedure (option I) illustrated in FIG. 2d, then the metal oxide layer 14* and the metal layer 15*, which were applied on the insulation layer 13 provided on the semiconductor substrate 12, are subjected to a thermal treatment at a temperature $T_1$ of e.g. greater than 600° C. (e.g. 600°–1000° C.) for a duration ti of e.g. 10-300 seconds by means of an RTA procedure (RTA=Rapid Thermal Annealing), in order to crystallize the, for example, amorphously applied, metal oxide layer 14*, i.e. to turn the thermally treated metal oxide layer 14 into an at least partially crystalline structure, and in order thermally to oxidize and crystallize the originally applied metal layer 15*, in order to obtain a thermally oxidized and crystallized metal layer 15 on the crystallized metal oxide layer 14. The metal oxide layer 14 and the metal layer 15, as applied (deposited) and thermally treated on the insulation layer 13 provided on the semiconductor substrate 12, thus form the layer sequence, respectively double layer 16, of the invention as an ion-sensitive layer structure for an ion-sensitive sensor.

In the option I illustrated in FIG. 2d, thus, the metal layer and the metal oxide layer lying therebeneath are both thermally oxidized as well as also crystallized at a temperature $T_1$ of, for example, greater than 600° C. for a duration $t_1$ of, for example, 10-300 seconds, in order to obtain the crystallized metal oxide layer 14 and the oxidized and crystallized metal layer 15 as layer sequence, respectively double layer 16.

Figure 2E:
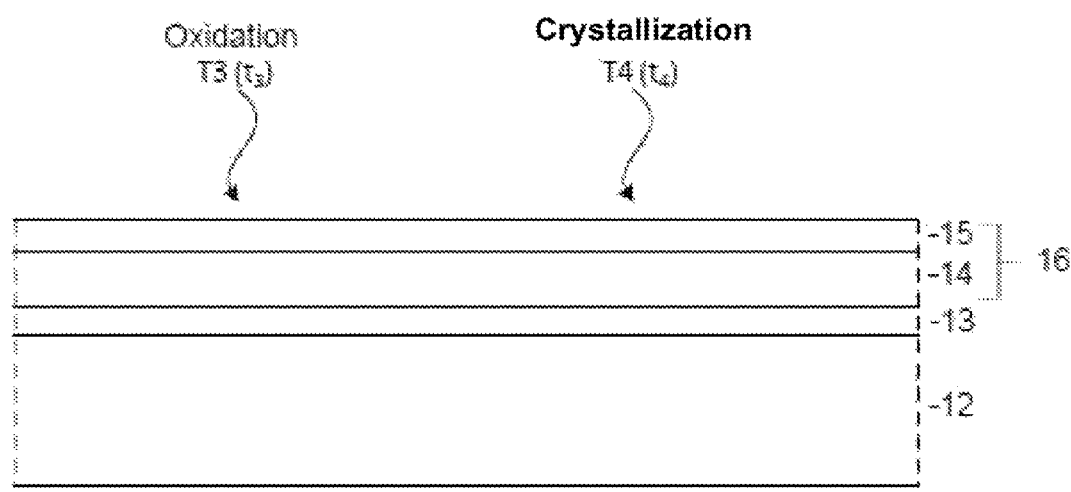

Alternatively, in the case of the optional procedure (option II) illustrated in FIG. 2e, the applied metal oxide layer 14* and the thereon applied metal layer 15* can, first of all, be thermally oxidized at an oxidation temperature $T_3$ of, for example, less than 550° C. (e.g. 300°–550° C.) for a duration $t_3$ of, for example, 10-300 seconds, whereupon, for example, subsequently at a temperature $T_4$ (crystallization temperature) of, for example, greater than 600° C. (e.g. 600°–1000° C.) for a duration $t_4$ of, for example, 10-300 seconds (by means of one or more RTA processes), a crystallization of the metal oxide layer 14* and the metal layer 15* is performed, in order to obtain the layer sequence, respectively double layer 16, with the crystallized metal oxide layer 14 and the oxidized and crystallized metal layer 15.

Figure 2F:
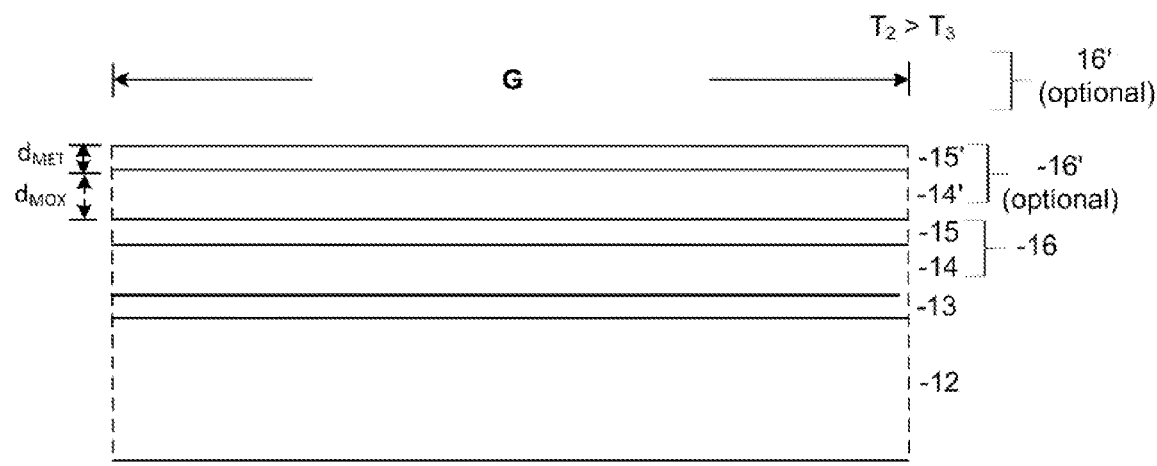

FIG. 2f shows an optional process step. Thus, corresponding to the procedure for producing the layer sequence, respectively double layer 16, illustrated in FIGS. 2b-e, correspondingly, one more or a plurality of additional double layers 16', 16" of a crystallized metal oxide layer 14' and an oxidized and crystallized metal layer 15' can be applied on the double layer 16.

Regarding the process steps illustrated based on FIGS. 2a-f, it should be heeded that the metal oxide layer(s) are, in each case, applied with a coating thickness $d_{MOX}$, which is greater than the coating thickness(es) of the thereafter applied metal layer(s) $d_{MET}$. Furthermore, the metal oxide layer(s) and the metal layer(s) have a compatible metal element (e.g. the same metal element).

The metal oxide layer(s) and the metal layer(s) can be applied, for example, by sputtering, vapor deposition, a CVD process (CVD=Chemical Vapor Deposition=chemical gas phase deposition), a PVD process (PVD=Physical Vapor Deposition) or an ALD process (ALD=Atomic Layer Deposition).

Optionally, after termination of the oxidative- and crystallization thermal treatments, a thermal post-treatment (an annealing procedure) can be performed, e.g. with an annealing temperature lower than the crystallization temperatures, for example, a temperature below 600° C., in order to achieve a so-called annealing of the crystalline, respectively crystallized, material structure of the layer sequence(s) 16, 16', wherein by means of such an annealing procedure, for example, the concentration of crystal defect locations and/or interstitial elements can be minimized and at least lessened.

As shown in FIG. 2f according to a further, optional process step (subsequent to the process step of FIG. 2d or FIG. 2e), corresponding to the procedure for producing the layer sequence, respectively double layer 16, described above with respect to FIGS. 2b-e, correspondingly another or a plurality of additional double layers 16', 16" of a crystallized metal oxide layer 14', 14" and an oxidized and crystallized metal layer 15', 15" can be applied on the double layer 16.

Regarding the process steps described based on FIGS. 2a-f, it should be heeded that the metal oxide layer(s) are applied, in each case, with a coating thickness $d_{MOX}$, which is greater than the coating thickness of the respectively thereafter applied metal layer $d_{MET}$. Furthermore, the metal oxide layer(s) and the metal layer(s) have a compatible metal element (the same metal element).

The metal oxide layer(s) and the metal layer(s) can be applied, for example, by sputtering, vapor deposition, a CVD process (CVD=Chemical Vapor Deposition=chemical gas phase deposition), a PVD process (PVD=Physical Vapor Deposition) or an ALD process (ALD=Atomic Layer Deposition).

Optionally, after termination of the oxidative- and crystallization thermal treatments, a thermal post-treatment (an annealing procedure) can be performed, e.g. with an annealing temperature lower than the crystallization temperatures, for example, a temperature below 600° C. (e.g. 300°-600° C.), in order to achieve a so-called annealing of the crystalline, respectively crystallized, material structure of the layer sequence(s) 16, 16', wherein, by means of such an annealing procedure, for example, the concentration of crystal defect locations and/or interstitial elements can be minimized and at least lessened.

Optionally, for example, as a preceding thermal treatment step, a thermal pretreatment at a temperature of >600° C. (e.g. between 300° C. and 600° C.) can be performed, in order, as already described above, first of all, to homogenize more strongly the layer-wise applied, still untempered materials of the layer sequence and in order, for example, to allow the interfaces between neighboring material layers to alloy and grow together more strongly with one another.

In the preceding, based on. FIGS. 2a-g, the process steps for producing the layer sequence, respectively another or a plurality of additional double layers 16', 16", of a crystallized metal oxide layer 14', 14" and an oxidized and crystallized metal layer 15', 15" on the double layer 16 were described.

Figure 2G:
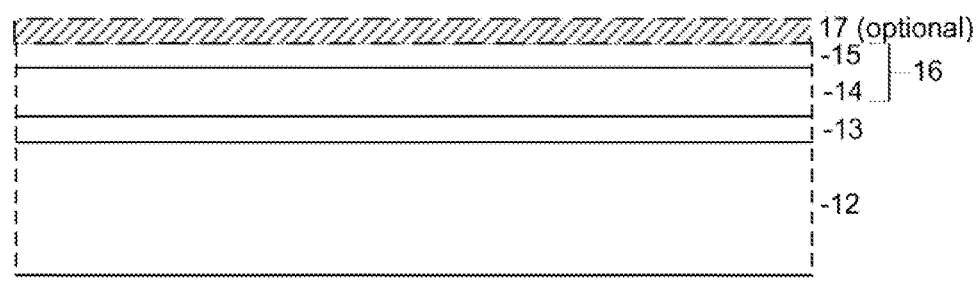

As presented in FIG. 2g as an optional further process step, a terminating protective layer 17 of a metal oxide material can now be deposited on the previously applied layer sequence of one or more double layers 16, respectively 16', 16", etc. In such case, this (thin) metal oxide, protective layer 17 can be deposited directly on the last metal layer 15, respectively 15', 15" etc. of the layer sequence 16, respectively 16', 16" etc., after these metal layers have been emplaced, i.e. in situ, without that this last metal layer was previously tempered. The thickness of the additional metal oxide, protective layer 17 can be between 3 and 70 nm (or between 3 and 50 nm).

Optionally, the protective layer 17 deposited as metal oxide can be deposited on the last metal layer oxidized, respectively oxidized and crystallized, by a thermal treatment, wherein the last protective layer 17 can have a thickness between 3 nm and 70 nm (or between 10 and 70 nm).

The applied, thin metal oxide, protective layer 17 and the last metal layer, respectively metal oxide layer, contain, in such case, a compatible (respectively the same) metal element.

Figure 1G:
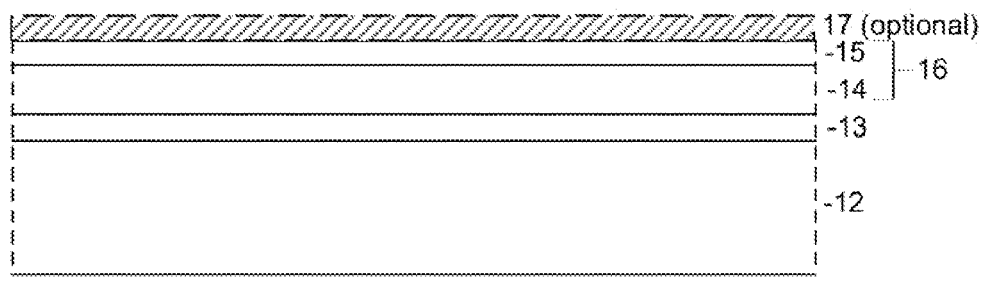

The providing of the metal oxide, protective layer 17 can, for the same reasons as already described based on FIG. 1g, have a positive effect on the operating properties of an ion-sensitive layer structure for an ion-sensitive sensor.

Figure 3:
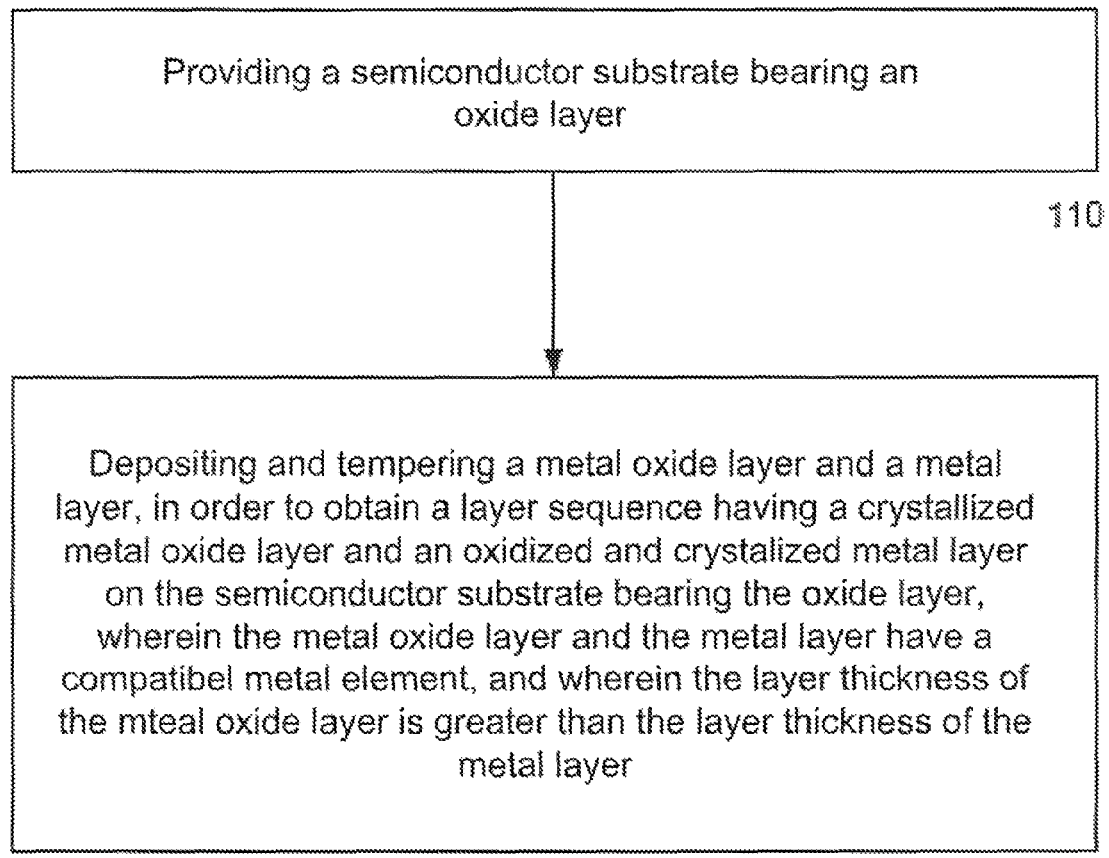
FIG. 3 is in principle, a flow diagram of a method for manufacturing an ion-sensitive structure according to an example of an embodiment of the present invention.

In the following, now, based on a flow diagram illustrated, in principle, in FIG. 3, a method 100 of the invention for manufacturing an ion-sensitive layer structure for an ion-sensitive sensor according to an example of an embodiment of the present invention will be explained.

In the method 100 of the invention, in a step 110, first of all, a semiconductor substrate 12 having an oxide layer 13 is provided. Then, in a step 120, a metal oxide layer 14* and a metal layer 15* are deposited and tempered, in order to obtain a layer sequence having a crystallized metal oxide layer 14 and an oxidized and crystallized metal layer 15 on the semiconductor substrate 12 bearing the oxide layer 13. In such case, the metal oxide layer 14 and the metal layer 15 have a compatible metal element, and the coating thickness $d_{MOX}$ of the metal oxide layer 14 is greater than the coating thickness $d_{MET}$ of the metal layer 15.

In a first optional procedure (option I) for performing step 120 for depositing and tempering a metal oxide layer 14* and a metal layer 15*, first of all, the metal oxide layer is deposited on the semiconductor substrate bearing the oxide layer. Thereupon, at least the metal oxide layer is tempered, in order to obtain a crystallized metal oxide layer. Thereupon, the metal layer is deposited on the crystallized metal oxide layer, whereupon the applied metal layer is tempered, in order to obtain an oxidized and crystallized metal layer.

In an additional optional procedure for performing step 120 for depositing and tempering a metal oxide layer and a metal layer, first the metal oxide layer is deposited on the semiconductor substrate bearing the oxide layer. Thereupon, the metal layer is deposited on the applied metal oxide layer, whereupon a thermal treatment of the applied metal oxide layer and the metal layer is performed, in order to obtain the crystallized metal oxide layer and the oxidized and crystallized metal layer on the semiconductor substrate bearing the oxide layer.

Corresponding to the above option 2, in the step of tempering, a first partial tempering can be performed at an oxidation temperature, in order to oxidize the applied metal layer. Furthermore, a second partial tempering at a crystallization temperature can be performed, in order to crystallize the applied metal oxide layer and the oxidized metal layer, in order to obtain the layer sequence with the crystallized metal oxide layer and the oxidized and crystallized metal layer.

Corresponding to the two above options 1 and 2, the step of applying and tempering a metal oxide layer and a metal layer can be repeated at least once, in order to obtain at least one other layer sequence having an additional crystallized metal oxide layer and an additional oxidized and crystallized metal layer on the first layer sequence, respectively double layer, wherein, in each case, the coating thickness of the additional metal oxide layer is (markedly) greater than the coating thickness of the additional metal layer. Furthermore, in each case, the metal oxide layer and the metal layer, respectively the other metal oxide layer and the other metal layer, have a compatible metal element, respectively the same metal element.

Through the application of the invention of a relatively thick buffer layer, respectively metal oxide layer, on the oxide layer provided on the semiconductor substrate, wherein on the metal oxide layer then a metal layer is applied with the same metal elements, it can be prevented that the material of the oxide layer is damaged by the metal deposition of the metal layer and its thermal treatment for oxidation, i.e. it can be prevented or at least lessened that, for example, the $SiO_2$ material of the gate insulator is damaged. It is true that the buffer layer, respectively metal oxide layer, on its surface facing, respectively interface with, the thereon lying metal layer is partially reduced, when the metal layer is subjected, for example, to the oxidative tempering, and oxygen atoms are transferred from the metal oxide layer to the adjoining metal layer. In this case, there arise, indeed, at the interface between the metal oxide layer and the metal layer, interface charges and/or so-called traps. Through the procedure of the invention of providing a metal oxide layer acting as buffer layer between the insulation layer (oxide layer) and the metal layer arranged thereon, the extent of the damage of the surface of the metal oxide layer, respectively buffer layer, compared with the case, in which the metal layer would be deposited directly on the oxide layer (insulation layer) provided on the semiconductor substrate, can at least be significantly lessened, even though a certain amount of damage, respectively degrading, of the metal oxide layer surface cannot be completely prevented. Since the metal oxide layer and the metal layer have a compatible metal element (the same metal element), the metal oxide material of the metal oxide layer and the metal material of the metal layer lie in thermodynamic equilibrium, in the case of which the oxygen can move reversibly, i.e. can be exchanged, between the two layers.

Furthermore, the metal oxide layer acting as buffer layer is produced with a sufficiently large coating thickness, in order to achieve that residual interface charges and traps remaining later after the oxidation and tempering of the metal material of the metal layer in, respectively at, the interface between the metal oxide layer and metal layer occur (relatively) far removed from the semiconductor/insulator interface. The metal oxide layer is thus effective, in order to function as a buffer layer, respectively spacing layer, between the insulation layer (the oxide layer provided on the semiconductor substrate) and the trap- and/or charge bearing interface between the metal oxide layer and the metal layer, so that disturbing influences on the working point of the active channel, for example, in an ISFET, or on the flat-band voltage in the case of an ion-sensitive, capacitively readable EIS sensor (with EIS structure), remain relatively small. According to the invention, it is thus enabled that the processing of the ion-sensitive layer structure coming in contact with the measured medium, especially the uppermost layer element exposed to the measured medium, provides, on the one hand, extremely stable material properties of the ion-sensitive layer structure and especially the uppermost layer, wherein simultaneously also the electrical properties satisfy extremely high demands.

Since in applying the metal oxide layer on the insulation layer ($SiO_2$ layer) provided on the semiconductor substrate, there are, respectively provided, inherently in the deposition procedure sufficient oxygen atoms, respectively oxygen, therefore no oxygen is withdrawn from the oxide material ($SiO_2$) of the oxide layer lying therebeneath, so that damage to the insulation layer by means of the procedure of the invention for manufacturing the ion-sensitive layer structure can be avoided. In examples of embodiments of the present invention, the metal layer is deposited as a thinner, respectively markedly thinner, layer than the metal oxide layer. In such case, for example, the metal layer can be deposited with a coating thickness, which is less than or equal to ½, ⅓, ¼ or ⅕, ..., ⅒ of the coating thickness of the previously applied metal oxide layer. The thinner forming of the metal layer compared with the metal oxide layer enables that the thermal oxidation of the metal layer remains manageable, since a thermal oxidation procedure of the terminating metal layer and the metal oxide layer lying therebeneath can be critical, if the metal layer and the metal oxide layer would have similar layer thicknesses. This results from the fact that the oxidation procedure is accompanied by a volume increase of the respective material, wherein the density of metal materials is almost always higher than that of metal oxide materials. Since now the oxygen in the case of the thermal oxidation of the metal material of the metal layer is positioned equally to the valences typical for metal oxide, while the oxygen in the case of the thermally reactive treating of the deposited metal oxide with the surrounding gaseous medium is replaced and rearranged, the molar space requirement in the case of a thermal oxidation procedure of the metal material is smaller, which leads again to denser layers than in the case of deposited metal oxides.

By means of the ion-sensitive structure, respectively ion-sensitive EIS structure, of the invention, compared to the previously used materials, an increased stability and sensitivity as regards the ions to be detected is obtained, wherein, furthermore, a low cross-sensitivity and a minimal drift coupled with good long term stability of a correspondingly formed sensor is achieved. Thus, vertical, respectively global, grain boundaries, which thermal treatments (tempering) bring about between the EIS structure, e.g. the gate-electrolyte interface and the oxide layer applied on the semiconductor substrate, respectively insulation layer (gate insulator, e.g. $SiO_2$), respectively the semiconductor bulk material (e.g. Si), can be prevented as much as possible, respectively interrupted, by the ion-sensitive EIS structure manufactured according to the invention.

The procedure of the invention for manufacturing an ion-sensitive layer structure can especially be used also for manufacturing an ion-sensitive field effect transistor ISFET.

Figure 4A:
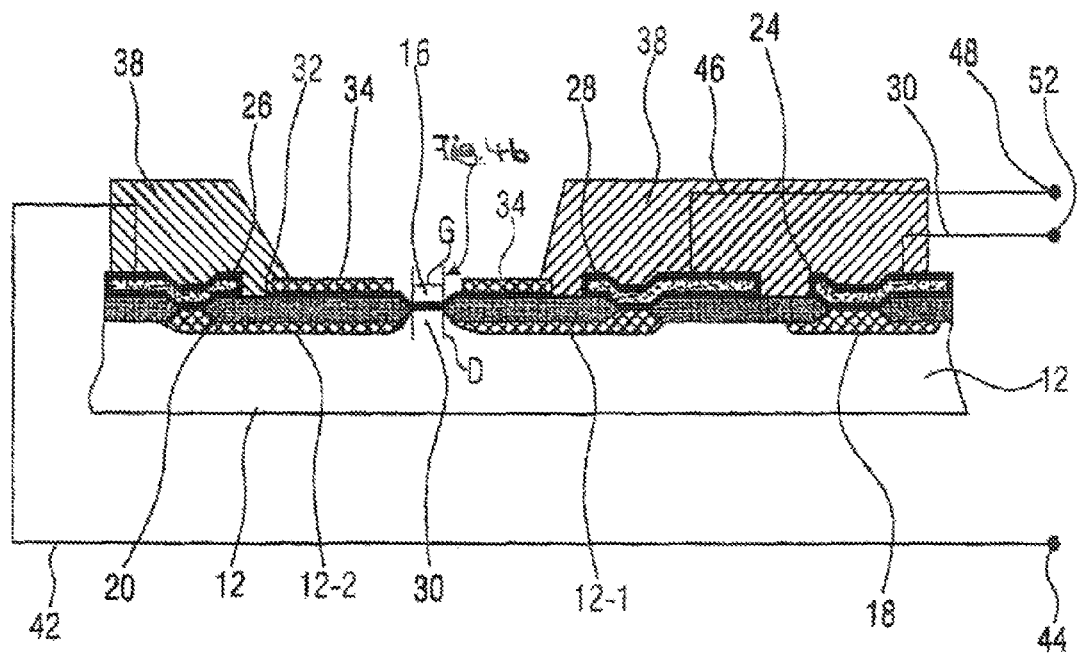
FIGS. 4a-4b are in principle, a cross sectional view of an example of an ion-sensitive field effect transistor with a detail view of an ion-sensitive layer structure for an ISFET according to an example of an embodiment of the present invention.
Figure 4B:
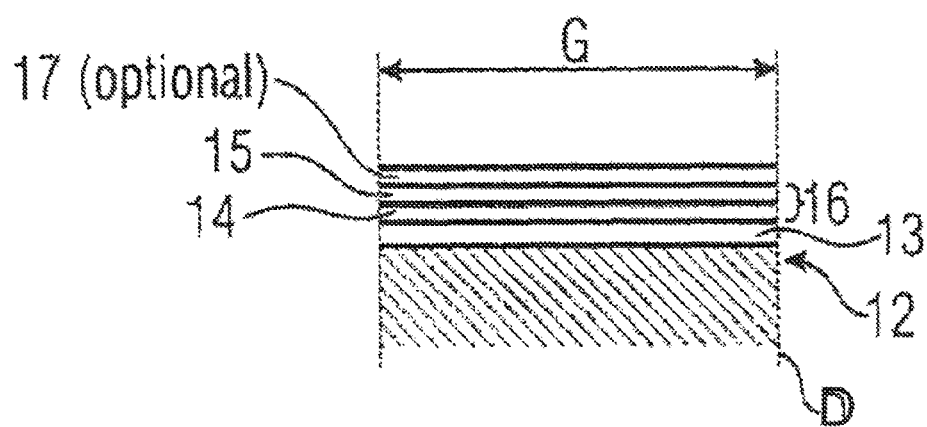

Thus, for example, with reference to the structure of an ISFET shown in FIGS. 4a-b, a source region and a drain region can be produced in a semiconductor substrate, respectively a semiconductor substrate is provided with a source region and a drain region. Finally, a gate region having an ion-sensitive layer structure can be produced, wherein this ion-sensitive layer structure can be produced corresponding to the procedure for manufacturing an ion-sensitive structure 16 for an ion-sensitive sensor as illustrated in FIGS. 1a-g and FIGS. 2a-g.

Equally, an ion-sensitive, capacitively readable EIS sensor having an ion-sensitive layer structure can be produced, in that the ion-sensitive layer structure is produced corresponding to the procedures illustrated in FIGS. 1a-g and FIGS. 2a-g. Equally, a light controlled, ion-sensitive sensor (LAPS sensor=Light Addressable Potentiometric Sensor) having an ion-sensitive layer structure can be produced, wherein this ion-sensitive layer structure can again be produced corresponding to the procedures illustrated in FIGS. 1a-g and FIGS. 2a-g for manufacturing an ion-sensitive structure for an ion-sensitive sensor.

In the following, the construction in principle and the operation in principle of an ion-sensitive sensor 10 will now be described based on FIG. 4a by way of example, e.g. in the form of an ISFET with use of an ion-sensitive EIS structure (EIS structure) 16 manufactured according to the invention.

In this connection, it is especially to be noted that the following description of the ion-sensitive structure 16 of the invention is essentially applicable to any ion-sensitive sensors, such as e.g. also capacitive, ion-sensitive sensors having an EIS structure, respectively to LAPS sensors. The ion-sensitive structure 16 based on FIGS. 4a and 4b of an ISFET 10 as ion-sensitive sensor is to be understood as purely by way of example.

FIG. 4a shows, by way of example, a cross sectional view of an ion-sensitive field effect transistor (ISFET) 10.

The ion-sensitive field effect transistor 10 includes a semiconductor substrate 12, e.g. a silicon substrate. Formed in the semiconductor substrate 12 is a source region 12-1 and a drain region 12-2. The substrate includes, furthermore, for example, a substrate connection region 18. The source region 12-1, the drain region 12-2 and the substrate connection region 18 can be embodied in the semiconductor substrate 12 as n- or p doped regions.

The semiconductor substrate 12 can be, for example, a combination of a substrate and, applied thereon, an epitaxial layer, in which the active regions of the FET component are formed, for example, by means of implantation processes.

Thus, for example, formed on a surface of the substrate 12 is a field oxide layer 20. Extending on the field oxide layer 20 is, for example, another insulating layer 16 (16', 16"). The ISFET 10 includes, furthermore, a connection contact 24, which extends through the field oxide layer 20 and the insulating layer 16 (in case the insulating layer 16 has a corresponding lateral expansion) and which is electrically connected with the substrate connection contact 18. Furthermore, the ISFET 10 includes a drain contact 26, which extends through the field oxide layer 20 and through the insulating layer 16 (optionally present there) and is electrically connected with the drain region 12-2. Furthermore, a source contact 28 is formed, which extends through the field oxide layer 20 and the insulating layer 16 (optionally present there) and is electrically connected with the source region 12-1.

Defined, respectively embodied during operation, between the source region 12-1 and the drain region 12-2 in the semiconductor substrate is a channel region 30. Above the channel region 30, a gate region G is formed, which has according to the invention the ion-sensitive structure, respectively EIS layer structure 16, for the ion-sensitive sensor (ISFET) 10, wherein the ion-sensitive layer structure 16 in the gate region G in the case of measuring e.g. a pH-value comes in direct contact with the measured medium. As shown in FIG. 4a, the ion-sensitive region, respectively the ion-sensitive layer structure 16, can be embodied coherently with the insulating layer. As was explained at length above regarding the method of the invention for manufacturing the ion-sensitive layer structure of the invention 16, and such as this is presented in FIG. 4b in enlarged view of the section D of FIG. 4a, the ion-sensitive layer structure of the invention in the gate region G is distinguished by the fact that applied on the semiconductor substrate 12 (e.g. a silicon-substrate) is an insulation layer 13 (e.g. $SiO_2$) as a substrate oxide, which has, for example, amorphous material properties, wherein deposited and tempered on this substrate oxide 12 is a metal oxide layer 14 and a metal layer 15, in order to obtain a layer sequence having a crystallized metal oxide layer 14 and an oxidized and crystallized metal layer 15 on the semiconductor substrate 12 provided with the oxide layer 13. In such case, the metal oxide layer and the metal layer have a compatible metal element, and the coating thickness $d_{MOX}$ of the metal oxide layer is (markedly) greater than the coating thickness $d_{MET}$ of the metal layer.

In FIG. 4a, the ISFET 10 includes, for example, a light blocking layer 34, which is formed on the insulating layer 32, in each case, laterally bordering, or neighboring, the gate region G. Formed on the drain contact 26 is, furthermore, for example, a passivating layer 38, which extends over the source contact 28 and the substrate connection contact 24 and which at least on the gate region G has an appropriate window. The drain contact 26 is connected, for example, via a line 42 having a drain-connection 44, while the source contact 28 is connected, for example, via a line 46 having a source-connection 48, and the substrate connection 24 is electrically connected, for example, via a line 50 having a substrate connection 52.

As presented enlarged in FIG. 4b, the layer sequence, respectively the double layer 16, includes, applied on the insulation layer 13, a crystallized metal oxide layer 14 having, in turn, a thereon applied, thermally oxidized and crystallized metal layer 15. In such case, the coating thickness $d_{MOX}$ of the metal oxide layer 14 is greater than the coating thickness $d_{MET}$ of the metal layer 15, wherein the metal oxide layer 14 and the metal layer 15 have a compatible metal element (e.g. tantalum, hafnium, zirconium, titanium or aluminum).

By means of the ion-sensitive structure, respectively ion-sensitive EIS structure, of the invention, which can be applied, for example, as gate structure, respectively gate material, for an ion-sensitive ISFET, there is obtained, compared with the previously used metal oxides, an improved stability and sensitivity as regards the ions to be detected, wherein, furthermore, a low cross-sensitivity and a minimal drift coupled with good long term stability can be achieved. Furthermore, there is obtained for an ion-sensitive sensor, using the ion-sensitive structure of the invention and a multilayer embodiment, a maximizing of the intrinsic material transitions. The ion-sensitive structure embodied as a layered stack can in the case of an ISFET form both the gate insulator as well as also the sensitive layer. By increasing the chemical stability of the sensitive layer, the working point of the ion-sensitive sensor can be so set that ion movement in the electrical field during sensor operation is minimized. In such case, also the field supported diffusing in of ions into the layer stack acting e.g. as gate insulator is lessened by the high number of interfacial stops.

Advantageous is, furthermore, that the ion-sensitive structure for an ion-sensitive sensor embodied according to the invention as a layer stack is manufacturable by means of CMOS compatible semiconductor manufacturing processes, wherein simultaneously the environmental compatibility of the corresponding manufacturing process can be guaranteed. According to the invention, furthermore, the required number of process substeps can be lessened and, thus, manufacturing costs decreased.

According to the invention, it is, furthermore, achieved that the structure changing interfaces inherent to the metal insulator materials, e.g. $HfO_2$, $ZrO_2$ etc. can be avoided during the vertical growth in the case of a layer deposition procedure and in the case of tempering for crystallization. In this way, furthermore, according to the invention, the conditions for an onset of vertical grain boundary formation in the metal oxide material, e.g. $HfO_2$ or $ZrO_2$, can likewise be prevented. The vertical grain boundaries, which thermal treatments (tempering) can cause between the EIS structure, e.g. the gate-electrolyte interface, and the oxide layer applied on the semiconductor substrate, respectively insulation layer, e.g. gate insulator (such as e.g. $SiO_2$), respectively the semiconductor bulk material (such as e.g. Si), can be avoided, respectively interrupted, as much as possible by the ion-sensitive EIS structure manufactured according to the invention.

The layering, respectively alternating sequence, of the layered stack can so occur according to the invention that interface dipoles are removed as much as possible by an inverting of the layer sequence. Furthermore, it becomes an option through the method of the invention for manufacturing an ion-sensitive structure not to have to leave the particular material system, whereby an extremely high pH-linearity of the respective ion-sensitive sensor can be achieved. Since, furthermore, the manufacture of the invention of the ion-sensitive structure as a layer stack can occur by means of usual semiconductor manufacturing processes, furthermore, the CMOS manufacturing compatibility and the environmental compatibility of the manufacturing process is assured.

The method of the invention for manufacturing an ion-sensitive layer structure for an ion-sensitive sensor, such as e.g. an ISFET, a capacitively readable EIS sensor or a LAPS sensor, can especially increase the service time in chemically aggressive media, such as e.g. in the case of a CIP procedure (CIP=Cleaning In Place) as well as in the case of relatively high temperatures. Thus, in the case of a correspondingly formed ion-sensitive sensor, such as e.g. an ISFET, the working point drift or also the flat-band voltage can be markedly lessened compared with conventionally embodied, ion-sensitive sensors under thermal sterilization conditions with hot steam, such as e.g. in the case of an SIP procedure (SIP=Sterilization In Place), e.g. in the case of temperatures of up to 135° C.

The invention claimed is:
1. A method for manufacturing an ion-sensitive structure for an ion-sensitive sensor, comprising the steps of:
providing a semiconductor substrate bearing an oxide layer; and
depositing and tempering a metal oxide layer and a metal layer, in order to obtain a layer sequence having a crystallized metal oxide layer and an oxidized and crystallized metal layer on the semiconductor substrate bearing the oxide layer, wherein:

the metal oxide layer and the metal layer have a same metal element; and the coating thickness (dMOX) of the metal oxide layer is greater than the coating thickness (dMET) of the metal layer.

2. The method as claimed in claim 1, wherein:
said step of depositing and tempering further comprises steps as follows:
depositing the metal oxide layer on the semiconductor substrate bearing the oxide layer, tempering at least the metal oxide layer, in order to obtain a crystallized metal oxide layer; depositing the metal layer on the crystallized metal oxide layer, and tempering the applied metal layer, in order to obtain an oxidized and crystallized metal layer.

3. The method as claimed in claim 1, wherein:
said step of depositing and tempering further comprises steps as follows:
depositing the metal oxide layer on the semiconductor substrate bearing the oxide layer;
depositing the metal layer on the applied metal oxide layer; and
tempering the applied metal layer and the applied metal oxide layer, in order to obtain the crystallized metal oxide layer and the oxidized and crystallized metal layer on the semiconductor substrate bearing the oxide layer.

4. The method as claimed in claim 3, wherein:
in said step of tempering, a first partial tempering is performed at an oxidation temperature, in order to oxidize the applied metal layer; and
a second partial tempering is performed at a crystallization temperature, in order to crystallize the applied metal oxide layer and the oxidized metal layer, in order to obtain the layer sequence with the crystallized metal oxide layer and the oxidized and crystallized metal layer.

5. The method as claimed in claim 1, wherein:
the metal oxide layer is applied with a thickness of 25 to 400 nm, and the metal layer is applied with a thickness of 1 to 100 nm on the metal oxide layer.

6. The method as claimed in claim 5, wherein:
the coating thickness for the applied metal oxide layer lies in a range of 50 to 200 nm; and
the coating thickness of the applied metal layer lies in a range between 3 and 30 nm.

7. The method as claimed in claim 1, further comprising the step of:
applying and tempering an additional metal oxide layer and an additional metal layer on the first layer sequence, in order to obtain another layer sequence having an additional crystallized metal oxide layer and an additional oxidized and crystallized metal oxide layer on the first layer sequence, wherein:
the coating thickness dMOX1 of the additional metal oxide layer is greater than the coating thickness of the additional metal layer dMET1; and
the first layer sequence and the second layer sequence have a same metal element.

8. The method as claimed in claim 1, further comprising the steps of:
repeating the step of applying and tempering a metal oxide layer and a metal layer a plurality of times, in order to obtain a plurality of double layer sequences having a crystallized metal oxide layer and an oxidized and crystallized metal layer applied thereon, wherein:
the coating thickness of the respective metal oxide layer is greater than the coating thickness of the respective metal layer; and
the applied layers have a same metal element.

9. The method as claimed in claim 8, wherein:
said steps of depositing and tempering are performed, in order to apply two to four other double layer sequences of a crystallized metal oxide layer and an oxidized and crystallized metal layer.

10. The method as claimed in claim 8, wherein:
a tempering is performed, in each case, after applying of a metal oxide layer or a metal layer, in order to obtain a crystallized metal oxide layer and/or an oxidized and crystallized metal layer.

11. The method as claimed in claim 8, wherein:
one or more layer sequences having a metal oxide layer and a metal layer are applied alternately to one another; and
said step of tempering is performed on the applied layers, in order to obtain a plurality of crystallized metal oxide layers and a plurality of oxidized and crystallized metal layers.

12. The method as claimed in claim 1, wherein:
said tempering is performed at a temperature of at least 600° C. as a crystallization procedure for producing the crystallized metal oxide layer and crystallized metal layer.

13. The method as claimed in claim 1, wherein:
a pretempering at an oxidation temperature below 600° C. is performed before the tempering at the crystallization temperature, in order to perform an oxidation procedure at least for the applied metal layer before the crystallization procedure.

14. The method as claimed in claim 1, wherein:
tantalum, hafnium, zirconium, titanium or aluminum is used as a metal element for the applied metal oxide layer or the applied metal oxide layers;
tantalum, hafnium, zirconium, titanium or aluminum is used as a metal element for the applied metal layer or the applied metal layers; and
the applied metal oxide layer or applied metal oxide layers and the applied metal layer or applied metal layers have a same metal element.

15. The method as claimed in claim 1, wherein:
the metal oxide layer or metal oxide layers and the metal layer or metal layers is/are applied by sputtering, vapor deposition, a CVD process, a PVD process or an ALD process.

16. The method as claimed in claim 1, wherein:
the oxide layer on the semiconductor substrate is obtained by means of a thermal oxidation procedure; and
the oxide layer provided on the semiconductor substrate has a coating thickness of 3 to 150 nm.

17. The method as claimed in claim 1, wherein:
the semiconductor substrate comprises n- or p doped silicon material; and
the oxide layer comprises an amorphous silicon dioxide material.

18. The method as claimed in claim 1, further comprising a step of:
applying a terminating layer before said step of tempering the applied metal layer and the applied metal oxide layer,
wherein the terminating layer is a metal oxide,
wherein the terminating layer is applied on the untempered metal layer, and
wherein the terminating layer and the metal layer have a same metal element.

19. The method as claimed in claim 18, further comprising a step of:
tempering the terminating layer, in order to obtain a crystallized, metal oxide, terminating layer.

20. The method as claimed in claim 19, wherein:

said step of tempering the terminating layer is performed together with the tempering of the applied metal layer, said step of depositing and tempering further comprises steps as follows:

a) depositing the metal oxide layer on the semiconductor substrate bearing the oxide layer, tempering at least the metal oxide layer, in order to obtain a crystallized metal oxide layer; depositing the metal layer on the crystallized metal oxide layer, and tempering the applied metal layer, in order to obtain an oxidized and crystallized metal layer, or b) together with the step of tempering the applied metal layer and the applied metal oxide layer, said step of depositing and tempering further comprises steps as follows: depositing the metal oxide layer on the semiconductor substrate bearing the oxide layer; depositing the metal layer on the applied metal oxide layer; and tempering the applied metal layer and the applied metal oxide layer, in order to obtain the crystallized metal oxide layer and the oxidized and crystallized metal layer on the semiconductor substrate bearing the oxide layer.

21. A method for manufacturing an ion-sensitive field effect transistor, comprising the steps of:

providing a semiconductor substrate having a source region and a drain region; and producing a gate region having an ion-sensitive layer structure, wherein:

the ion-sensitive layer structure is produced according to a method as claimed in claim 1.

22. A method for the read out of an ion-sensitive, capacitively readable, EIS sensor having an ion-sensitive layer structure, wherein the ion-sensitive layer structure is produced according to a method as claimed in claim 1.

23. A method for manufacture of a light operated, ion-sensitive sensor having an ion-sensitive layer structure, wherein the ion-sensitive layer structure is produced according to a method as claimed in claim 1.

24. An ion-sensitive sensor having an ion-sensitive structure, wherein the ion-sensitive structure is obtained by a method as claimed in claim 1.

25. The ion-sensitive sensor as claimed in claim 24 and embodied as an ISFET element, capacitively readable EIS element or LAPS element.

* * * * *